(12) United States Patent
Matthison-Hansen et al.

(10) Patent No.: US 11,357,392 B2
(45) Date of Patent: Jun. 14, 2022

(54) BENDING SECTION FOR AN ENDOSCOPE

(71) Applicant: AMBU A/S, Ballerup (DK)

(72) Inventors: Kaspar Mat Matthison-Hansen, Helsingør (DK); Morten Jacobsen, Hørsholm (DK)

(73) Assignee: AMBU A/S, Ballerup (DK)

( * ) Notice: Subject to any disclaimer, the term of this patent is extended or adjusted under 35 U.S.C. 154(b) by 263 days.

(21) Appl. No.: 16/623,960

(22) PCT Filed: Jun. 25, 2018

(86) PCT No.: PCT/EP2018/066916
§ 371 (c)(1),
(2) Date: Dec. 18, 2019

(87) PCT Pub. No.: WO2019/002186
PCT Pub. Date: Jan. 3, 2019

(65) Prior Publication Data
US 2020/0138268 A1    May 7, 2020

(51) Int. Cl.
*A61B 1/005* (2006.01)
*A61B 1/06* (2006.01)

(52) U.S. Cl.
CPC .......... *A61B 1/0055* (2013.01); *A61B 1/0052* (2013.01); *A61B 1/0057* (2013.01); *A61B 1/0676* (2013.01); *A61B 1/0684* (2013.01)

(58) Field of Classification Search
CPC .... A61B 1/0055; A61B 1/0052; A61B 1/0057
See application file for complete search history.

(56) References Cited

U.S. PATENT DOCUMENTS 4,580,551 A * 4/1986 Siegmund ............ A61B 1/0055
600/139
4,651,718 A   3/1987 Collins
(Continued)

FOREIGN PATENT DOCUMENTS

CN   103228199 A   7/2013
EP   0 183 585     6/1986
(Continued)

OTHER PUBLICATIONS

Exam Report issued in Denmark Patent App. No. 2017 70501, dated Nov. 27, 2017, 9 pages.
(Continued)

*Primary Examiner* — Alexandra L Newton
*Assistant Examiner* — Rynae E Boler
(74) *Attorney, Agent, or Firm* — Faegre Drinker Biddle & Reath LLP (57) ABSTRACT

A bending section (5) for an endoscope (1) and the endoscope, where the bending section comprises a number of segments (12), where adjacent segments are connected by a first hinge (14) and a second hinge (24). Both the first and the second hinges are made integrally from the same material as the segments (12), and the first and second hinges are arranged for allowing the connected segments to bend in a bending plane. A second hinge at the distal end of a segment forms a continuous rib (44) with the second hinge (24) at the proximal end of the segment. This continuous rib is arranged perpendicular to the bending plane.

24 Claims, 5 Drawing Sheets

(56) References Cited

U.S. PATENT DOCUMENTS

| | | | |
|---|---|---|---|
| 4,706,653 A | 11/1987 | Yamamoto | |
| 4,745,470 A | 5/1988 | Yabe et al. | |
| 4,778,247 A | 10/1988 | Carpenter | |
| 4,832,003 A | 5/1989 | Yabe | |
| 4,856,495 A | 8/1989 | Tohjoh et al. | |
| 4,860,732 A | 8/1989 | Hasegawa et al. | |
| 4,911,148 A | 3/1990 | Sosnowski et al. | |
| 4,918,521 A | 4/1990 | Yabe et al. | |
| 5,089,895 A | 2/1992 | Fraker et al. | |
| 5,176,126 A | 1/1993 | Chikama | |
| 5,376,960 A | 12/1994 | Wurster | |
| 5,379,756 A | 1/1995 | Pileski et al. | |
| 5,418,566 A | 5/1995 | Kameishi | |
| 5,438,975 A | 8/1995 | Miyagi et al. | |
| 5,547,457 A | 8/1996 | Tsuyuki et al. | |
| 5,830,401 A | 11/1998 | Prichard et al. | |
| 5,966,168 A | 10/1999 | Miyazaki | |
| 6,004,263 A | 12/1999 | Nakaichi | |
| 6,110,104 A | 8/2000 | Suzuki et al. | |
| 6,302,616 B1 | 10/2001 | Takahashi | |
| 6,456,863 B1 | 9/2002 | Levin et al. | |
| 7,455,806 B2 | 11/2008 | Junger et al. | |
| 7,758,495 B2 | 7/2010 | Pease et al. | |
| 8,182,422 B2 | 5/2012 | Bayer et al. | |
| 8,547,424 B2 | 10/2013 | Ishii et al. | |
| 8,790,250 B2 | 7/2014 | Petersen et al. | |
| 9,125,582 B2 * | 9/2015 | Petersen | A61B 1/0684 |
| 9,220,400 B2 | 12/2015 | Petersen | |
| 9,486,595 B2 | 11/2016 | Borrye et al. | |
| 9,572,482 B2 | 2/2017 | Lin | |
| 9,622,649 B2 | 4/2017 | Lin | |
| 10,321,804 B2 | 6/2019 | Jacobsen et al. | |
| 2002/0022765 A1 | 2/2002 | Belson | |
| 2003/0056540 A1 | 3/2003 | Mukasa et al. | |
| 2004/0143276 A1 | 7/2004 | Sturtz et al. | |
| 2004/0199052 A1 | 10/2004 | Banik et al. | |
| 2004/0242963 A1 | 12/2004 | Matsumoto | |
| 2005/0070759 A1 | 3/2005 | Armstrong | |
| 2005/0075538 A1 | 4/2005 | Banik et al. | |
| 2005/0107667 A1 | 5/2005 | Danitz et al. | |
| 2005/0131279 A1 | 6/2005 | Boulais | |
| 2005/0140068 A1 | 6/2005 | Junger et al. | |
| 2005/0154262 A1 | 7/2005 | Banik et al. | |
| 2005/0119527 A1 | 9/2005 | Ellis et al. | |
| 2005/0203341 A1 | 9/2005 | Welker et al. | |
| 2005/0234499 A1 | 10/2005 | Olson et al. | |
| 2006/0173243 A1 | 8/2006 | Watanabe | |
| 2006/0178556 A1 | 8/2006 | Hasser et al. | |
| 2007/0049800 A1 | 3/2007 | Boulais | |
| 2007/0129466 A1 | 6/2007 | Kagawa et al. | |
| 2007/0249896 A1 | 10/2007 | Goldfarb et al. | |
| 2007/0249907 A1 | 10/2007 | Boulais | |
| 2008/0114205 A1 | 5/2008 | Kagawa et al. | |
| 2008/0194911 A1 | 8/2008 | Lee | |
| 2008/0221393 A1 | 9/2008 | Padget | |
| 2008/0249483 A1 | 10/2008 | Slenker | |
| 2008/0268559 A1 | 10/2008 | Jung | |
| 2008/0287741 A1 | 11/2008 | Ostrovsky | |
| 2008/0287963 A1 * | 11/2008 | Rogers | A61B 1/00042 606/130 |
| 2009/0054728 A1 | 2/2009 | Trusty | |
| 2009/0093679 A1 | 4/2009 | Suigetsu | |
| 2009/0177040 A1 | 7/2009 | Lyons | |
| 2009/0209819 A1 | 8/2009 | Kitagawa et al. | |
| 2010/0210905 A1 | 8/2010 | Takeuchi et al. | |
| 2010/0217082 A1 | 8/2010 | Ito et al. | |
| 2010/0262180 A1 | 10/2010 | Danitz et al. | |
| 2010/0280316 A1 | 11/2010 | Dietz et al. | |
| 2010/0324367 A1 | 12/2010 | Matsumoto et al. | |
| 2011/0034771 A1 | 2/2011 | Konstorum | |
| 2011/0230718 A1 | 9/2011 | Akui | |
| 2011/0251519 A1 | 10/2011 | Romoscanu | |
| 2012/0002981 A1 | 2/2012 | Frassica et al. | |
| 2012/0029281 A1 | 2/2012 | Frassica et al. | |
| 2012/0165608 A1 | 6/2012 | Banik et al. | |
| 2013/0245376 A1 | 9/2013 | Oku | |
| 2013/0331730 A1 | 12/2013 | Fenech et al. | |
| 2014/0114129 A1 | 4/2014 | Peh | |
| 2014/0142388 A1 | 5/2014 | Suzuki | |
| 2014/0243592 A1 | 8/2014 | Kato et al. | |
| 2015/0335227 A1 * | 11/2015 | Jacobsen | A61B 1/00114 600/110 |
| 2015/0366436 A1 | 12/2015 | Iuel | |
| 2016/0101254 A1 | 4/2016 | Hansen | |
| 2017/0028684 A1 | 2/2017 | Imai et al. | |
| 2020/0196835 A1 | 6/2020 | Qvist et al. | |
| 2020/0268238 A1 | 8/2020 | Jensen et al. | |
| 2020/0281445 A1 | 9/2020 | Matthison-Hansen et al. | |

FOREIGN PATENT DOCUMENTS

| | | |
|---|---|---|
| EP | 1 927 312 | 6/2008 |
| EP | 2 949 262 | 12/2015 |
| JP | 06-189898 A | 7/1994 |
| JP | 2 948722 | 9/1999 |
| JP | 2002-224019 A | 8/2002 |
| JP | 2005-152043 A | 6/2005 |
| KR | 10-2012-0056363 A | 6/2012 |
| WO | 2007/124211 A2 | 11/2007 |
| WO | 2009/029639 A1 | 3/2009 |
| WO | 2010/066787 A1 | 6/2010 |
| WO | 2010/066788 A2 | 6/2010 |
| WO | 2010/066789 A1 | 6/2010 |
| WO | 2010/066790 A1 | 6/2010 |
| WO | 2010/067765 A1 | 6/2010 |
| WO | 2014/106510 A1 | 7/2014 |
| WO | 2014/106511 A1 | 7/2014 |
| WO | 2016/188537 A1 | 12/2016 |
| WO | 2016/188538 A1 | 12/2016 |
| WO | 2016/188539 A1 | 12/2016 |
| WO | 2016/188540 A1 | 12/2016 |
| WO | 2016/188541 A1 | 12/2016 |
| WO | 2016/188542 A1 | 12/2016 |
| WO | 2016/188543 A1 | 12/2016 |

OTHER PUBLICATIONS

Search report in related European application No. 18 734 196.1 dated May 12, 2021, 5 pgs.

International Search Report in related PCT application No. PCT/EP2018/0066916 dated Oct. 10, 2018, 3 pages Extended Search Report in related EPO application No. EP 18 215 278 dated Jun. 5, 2019, 7 pages.

Extended Search Report in related EPO application No. EP 19160528 dated Sep. 2, 2019, 7 pages.

In corresponding International Application No. PCT/DK2013/050002, International Search Report, dated Sep. 12, 2013; 2 pages and International Preliminary Report on Patentability; dated Jul. 7, 2015; 7 pages.

International Preliminary Report on Patentability received for PCT Patent Application No. PCT/DK2013/050002, dated Jul. 16, 2015, 8 pages.

International Preliminary Report on Patentability received for PCT Patent Application No. PCT/EP2018/066916, dated Jan. 9, 2020, 7 pages.

International Search Report and Written Opinion received for PCT Patent Application No. PCT/DK2013/050002, dated Sep. 12, 2013, 9 pages.

* cited by examiner

BENDING SECTION FOR AN ENDOSCOPE

CROSS-REFERENCE TO RELATED APPLICATIONS

This application is a National stage application filed under 35 U.S.C. § 371 of International Application No. PCT/EP2018/066916, filed on Jun. 25, 2018, which claims the benefit of Danish Patent Application No. PA 2017 70501, filed on Jun. 26, 2017, which applications are incorporated herein by reference in their entirety.

This invention is related to endoscopes, and in particular to a bending section for an endoscope, where the bending section comprises a number of segments, where adjacent segments are connected by a first hinge and a second hinge, both the first and the second hinges being made integrally from the same material as the segments.

Endoscopes are known for visual inspection of inaccessible places such as human body cavities. Typically, the endoscope comprises an insertion cord connected to an operating handle at the proximal end and visual inspection means, such as a built in camera, at the distal end of the insertion cord. Electrical wiring for the camera and other electronics such as LED lighting run along the inside of the insertion cord from the handle to the tip at the distal end.

In order to be able to maneuver the endoscope inside a body cavity, the distal end of the endoscope may comprise a section with increased flexibility, e.g. a bending section. Typically, the bending section is controlled from the control handle by tensioning or slacking pull wires running along the inside insertion cord from the bending section to a control mechanism at the control handle. Furthermore, a working channel may run along the inside of the insertion cord from the handle via the bending section to the tip, e.g. allowing liquid to be removed from the body cavity or allowing the insertion of surgical instruments or the like into the body cavity.

WO 2014/106511 A1 discloses a bending section for an endoscope. In this bending section adjacent segments are connected by three hinges, made from the same material as the segments and manufactured in the same molding process as the segments, so that the bending section is a one-piece construction. These hinges are shown to have a relatively small cross sectional area, and to be relatively narrow measured in a direction extending perpendicular and radially to a longitudinal axis of the bending section. This configuration results in a bending section with limited torsional and longitudinal stiffness.

It is desirable with a bending section which allows maneuvering the tip of the endoscope to its extreme positions, i.e. maximum bending and exerting some force, without a risk of impairing the performance of the bending section, e.g. by displacement of a hinge due to a plastic deformation in the material. Furthermore, it is desirable if the performance of the bending section is maintained even if it is exposed to a force in a direction perpendicular to the plane of bending. The maneuverability of the bending section and the force on e.g. the hinges is further challenged when a tool is arranged in the working channel of the endoscope.

With a view to the above, it is an objective of the present invention to provide a bending section of the above mentioned type with improved torsional and longitudinal stiffness. This should preferably be achieved without having to apply more force for the bending. Also, the space available for a possible working channel should preferably not be reduced.

It has now been found that this problem can be solved by providing a bending section wherein the first and second hinges are arranged for allowing the connected segments to bend in a bending plane, wherein a second hinge at the distal end of a segment forms a continuous rib, perpendicular to the bending plane, with the second hinge at the proximal end of the segment. This improves the longitudinal and torsional stiffness, because the continuous rib will serve as an anchoring point for the second hinges, which can then be made wider than in the prior art.

Here, the bending plane is understood as the plane in which two adjacent segments will bend. In the case of a two-way bending section, this bending plane will also be the overall bending plane of the bending section as such. There may be exactly two hinges between two adjacent segments through the whole bending section or for a part of the bending section. There could also be more than two hinges between two adjacent segments through the whole bending section or for a part of the bending section.

In an embodiment of the bending section a first width is defined for the first hinge in a direction perpendicular to the bending plane, and a second width is defined for the second hinge in a direction perpendicular to the bending plane, wherein the second width is at least a factor of two larger than the first width. This provides a mechanical strong and stable bending section.

In an embodiment of the bending section the first and second hinges are placed in mutual opposite or approximately opposite directions from a center axis of the bending section, and the first and second width are extending in a radial direction from the center axis. This has the advantage of providing a stable bending section with similar bending properties in both bending directions.

In a further embodiment a diameter line can be defined for the bending section. This diameter line is passing through the center axis of the bending section, and the diameter line can be placed between two segments to pass both the first and the second hinge. This diameter line is applied for describing the position of the two hinges in relation to a center axis of the bending section, and not to define a measured value of the bending section diameter. The width of the first and second hinges will also be measured along this diameter line.

In an embodiment of the bending section, the bending section including segments and hinges has been molded as a one-piece construction. This may be in one piece from one material, or it could be in one piece but from e.g. two materials, such as by a two component molding process. The applied material is preferably a plastic material. This provides for a simpler and thereby cheaper production, and is especially an advantage when the bending section is to be applied with a single use endoscope.

In an embodiment of the bending section, the bending section comprises a passage through each segment, this passage is adapted to accommodate a working channel of the endoscope. The passage being arranged such that it passes between the first hinge and the second hinge. This provides a symmetrical bending section, giving the same bending properties in the two directions, in the case of a two way bending section.

In an embodiment of the bending section, the width of the second hinge, named the second width, is at least a factor of three larger than the first width, preferably the second width is a factor of four larger than the first width. This has been found to result in an even more stable bending section.

In an embodiment of the bending section, the second width varies as function of the position in a longitudinal direction from the distal end segment towards the proximal end segment. This can be applied for achieving differences in bending performance between different sets of segments. In a further embodiment the second width is smaller for a second hinge located close to either the distal end segment or the proximal end segment, compared to the second width of second hinges arranged in the middle of the bending section. This may provide some advantages in the process of molding the bending section.

In an embodiment of the bending section, the second width of the second hinges is the same or substantially the same between all segments of the bending section. This will give the same bending performance between all segment of the bending section, and thereby a predictable overall bending performance of the bending section In an embodiment of the bending section, the second hinge separates two passages adapted for arrangement of electrical wires. This leaves two well-defined spaces for the wires. The wires may be arranged in two bundles before arranging them in the bending section.

In a second aspect, the invention is directed at an endoscope comprising a bending section according to any one of the embodiments described above. In a further embodiment this endoscope is adapted for single use. By single use is meant that the endoscope is discarded after having been use for one patient.

In a third aspect, the invention is directed at an endoscope system comprising a monitor and an endoscope according to the above described endoscope.

Embodiments of the invention will in the following be described in more details with reference to the figures, wherein.

Figures 1, 2:
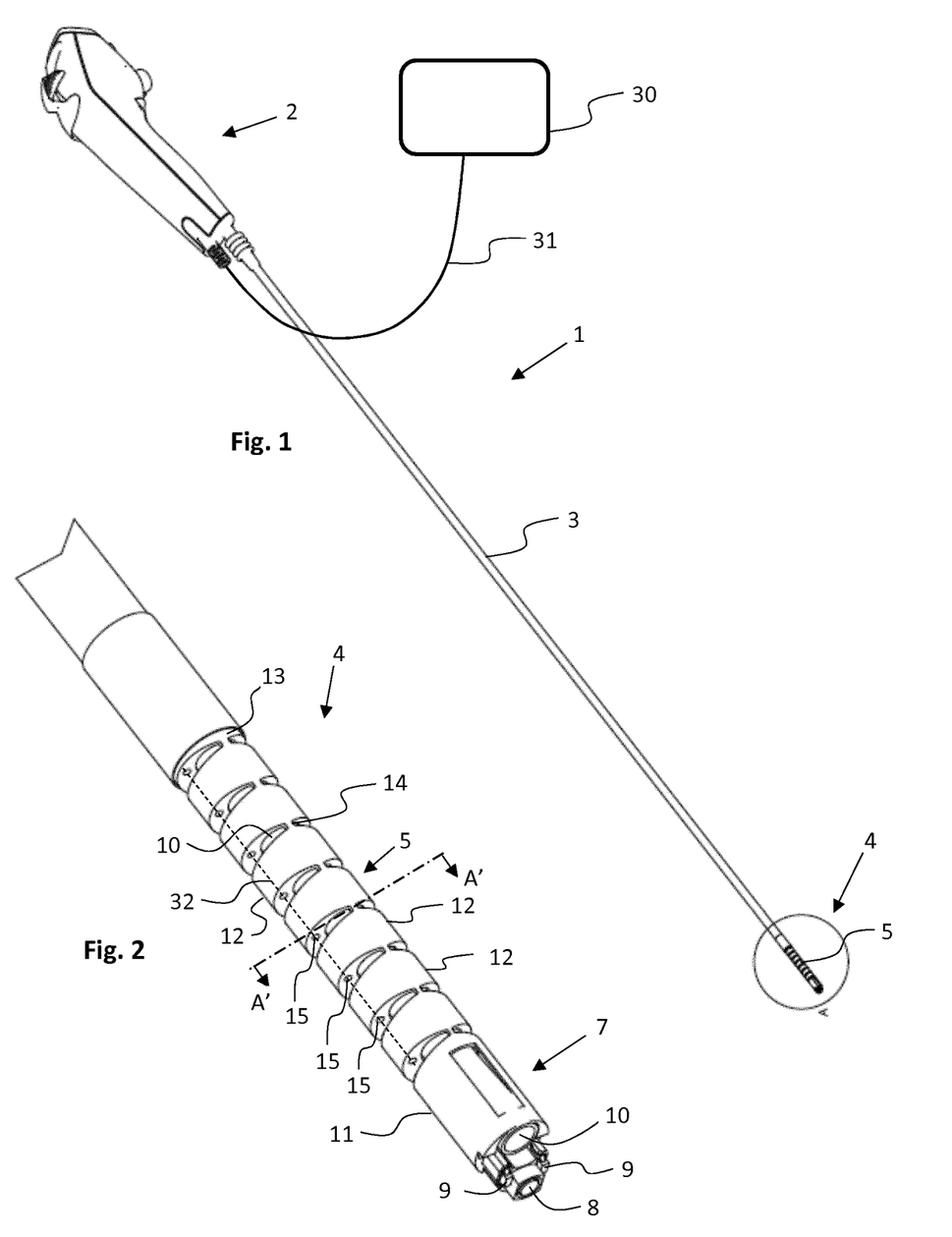
FIG. 1 illustrates a perspective view of an endoscope with a bending section.
FIG. 2 illustrates a perspective view of a distal end of the endoscope including a bending section.

FIG. 1 shows an endoscope 1 having a control handle 2, an insertion cord 3 comprising a distal end 4 and a bending section 5. Also, a monitor 30 for displaying the image seen by a camera 8 (see FIG. 2) is shown. The monitor may be connected to the handle 2 by a cable 31. The control handle 2 is here provided with a control lever which enables an operator of the endoscope 1 to control the bending of the bending section 5 through e.g. two pull wires, which by being tensioned or slacked can bend the bending section in one plane, but into two opposite directions. The bending of the bending section could alternatively be controlled by one or more steering wires which can be pulled and pushed alternately, whereby one steering wire may bend the bending section in two directions.

FIG. 2 shows a closer view of the distal end 4 with the bending section 5 and the distal tip 7. Here, the bending cover normally protecting the bending section is not shown in order to clearly show the bending section. Also, the molding plastic material for the distal tip is not included in FIG. 2. The distal tip 7 comprises a camera 8, light emitting diodes 9 and an opening or passage 10 for a working channel. The working channel may be used for irrigation or removal of liquid, or for the introduction of a tool e.g. for specimen collection.

The bending section 5 is comprised of a number of sections including a distal end segment 11 forming part of the distal tip 7, and a proximal end segment 13 connected to the rest of the insertion cord 3. Furthermore, a number of segments 12 are arranged between the distal end segment 11 and the proximal end segment 13. The segments 11, 12, 13 are interconnected by hinges 14. These hinges 14 are preferably integrally made from the same material as the segments 12, and preferably the hinges and the segments 11, 12, 13 form a single continuous piece of material. Examples of materials could be polypropylene, polyacetal (POM) or a semi-aromatic polyamide (nylon).

FIG. 2 further shows that the working channel 10 also seen at the distal tip, continues all the way through the bending section 5. The working channel 10 comprises a tubing which is arranged in a passage 33 (see FIGS. 3 and 4) in order to form a working channel which is tight to liquids etc.

FIG. 2 also indicates holes 15 for the positioning of the pull wires (the pull wires are not shown). The pull wires are arranged inside guide tubes, thereby forming Bowden cables along the distance from the control handle 2 to the proximal segment 13 of the bending section. The guide tubes terminate at the proximal segment 13, and the pull wires continues through the holes 15 in the bending section. These holes 15 forms a guiding channel for the pull wires, and are preferably placed close to the outer periphery of the bending section. The pull wires are secured to the distal segment 11 or in the distal tip 7. This configuration together with the hinges 14 allows for the bending of the bending section by tensioning one pull wire and slacking the other.

Figure 3:
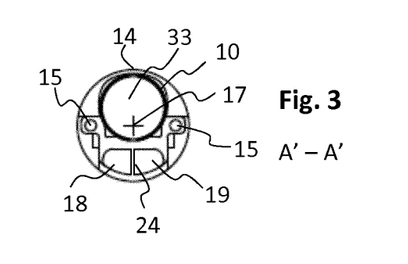
FIG. 3 illustrates a cross-sectional view through a segment of a bending section.

FIG. 3 shows a cross-sectional view (A'-A' in FIG. 2) of a bending section. The longitudinal center axis is indicated by a cross 17. The passage 10 for the working channel is also shown. This will often have a circular shape. Holes 15 for the pull wires are also seen. These are often arranged in opposite directions from the longitudinal center axis 17, and will extend in parallel to this axis. In the top of the passage 10 a first hinge 14 is arranged between each of the segments 12.

Two further passages 18, 19 are illustrated in the cross-sectional view in FIG. 3. These passages 18, 19 are adapted to accommodate e.g. electrical wires for transferring power and signals between the control handle 2 and the camera, lightning and electronics in the distal tip 4. These two passages are separated by a hinge 24 referred to as a second hinge.

Figure 13:
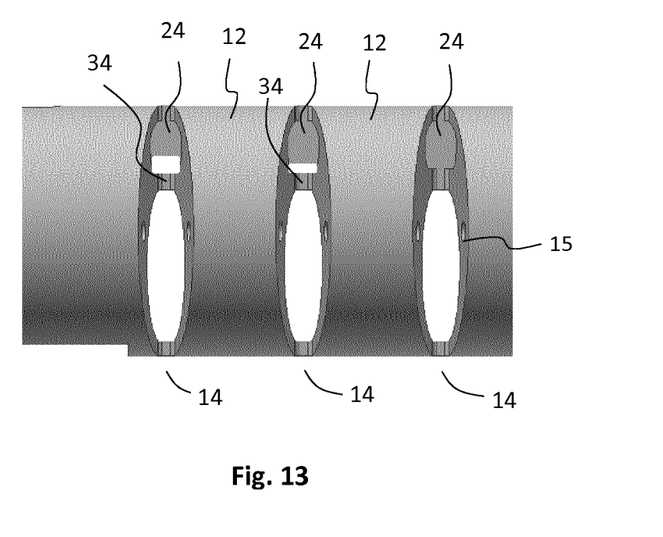
FIG. 13 illustrates an embodiment of a bending section where the second hinges have a varying width.

This second hinge 24 will form a connection between the segments. The second hinge 24 at the distal end of a segment 12 is forming a continuous rib 44 (shown in FIG. 10), with the second hinge at the proximal end of the segment, providing at least partially a reinforcing partition between the passages 18, 19 increasing the overall strength of the bending section 5. This continuous rib 44 is arranged in a plane perpendicular to the bending plane. The first hinge 14 and the second hinge 24 may be the only connection between adjacent segments 12 of the bending section. However, some embodiments may comprise more than two hinges between adjacent segments. An example of such an embodiment is shown in FIG. 13.

The continuous rib 44 is preferably formed as a sheet layer of material which also forms the second hinge 24. The continuous rib will extend in a plane perpendicular to or substantially perpendicular to the bending plane. This continuous rib 44 is thus contiguous with the second hinges 24, and will preferably continue through several segments 12 of the bending section 5 and have the same or substantially the same thickness both when the rib 44 forms a second hinge 24 and when the rib 44 forms the connection of two second hinges through a segment 12 of the bending section. The rib will separate the two passages 18, 19, which are formed in each segment 12 and continue through the whole bending section 5. The rib can thus be described as a continuous sheet layer extending through several bending section segments 12 and forming second hinges 24 between these segments.

Typically, the first hinge 14 together with the second hinge 24 forms a hinge plane which may pass through the center axis 17. The holes 15 for the pull wires going through the segments, are extending along two lines (one such line 32 is shown in FIG. 2). These two lines of holes 15 extends in a longitudinal direction of the bending section, when the bending section is in a non-bended, i.e. neutral, position. The two lines of holes will form a pull wire plane which may also pass through the center axis 17. The pull wire plane will also be the plane in which the bending section is bending when manipulating the pull wires. Typically, the hinge plane will extend perpendicular to the pull wire plane, while the pull wire plane will be parallel with or coincident with the bending plane.

Figures 4, 5:
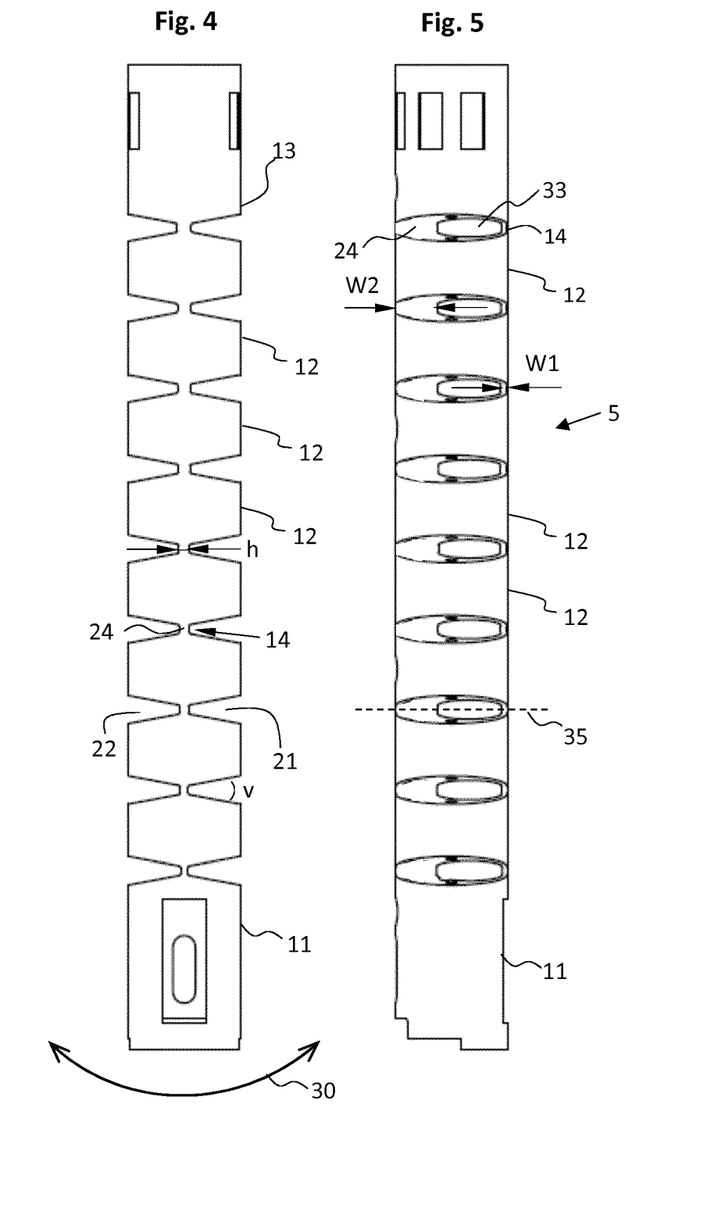
FIG. 4 illustrates a side view of a bending section where the plane with hinges is perpendicular to the plane of the paper.
FIG. 5 illustrates a side view of the bending section of FIG. 4 rotated 90 degrees around a longitudinal axis.

FIG. 4 shows a side view of a bending section where the plane with hinges is perpendicular to the plane of the paper. I.e. the hinges 14, 24 are all seen as placed in the centerline of the bending section, and being the only connection between the segments 12. FIG. 4 further shows a number of wedge formed spaces 21, 22 between the segments 12. These wedge formed spaces 21, 22 will allow for bending of the bending section. When the bending section is in the neutral (straight) position, as in FIG. 4, the angle of the wedge formed spaces is v as indicated. When the bending section is bending the angle v will be smaller on one side and larger on the opposite side. The angle v together with the total number of segments is decisive for the overall bending performance of the bending section, including the maximum bending angle and the bending radius.

The number of segments in a bending section could for example be in the range 10-24, such as in the range 12-20. The figures show a lower number of segments for clarity reasons. The bending radius of the bending section would often be in a range of 8-17 mm. measured to the center axis of the bending section. Preferably, the bending radius will often be in the range 10-15 mm.

The curve shaped double arrow 30 at the bottom of FIG. 4 indicates the direction of bending when the bending section shown in FIG. 4 is bending. The height h of the hinges is also indicated in FIG. 4. The height h may be the same for all hinges in the bending section, and the height could then be in a range of e.g. 0.2-0.5 mm. As indicated in FIG. 4 the height may also increase when moving from the distal end towards the proximal end of the bending section as also suggested in WO 2014/106511 A1. However, the hinges between two specific segments will preferably have the same height h.

FIG. 5 shows the bending section 5 of FIG. 4 rotated 90 degrees around the longitudinal axis. The hinges 14, 24 are here shown between the segments 12. Also, a passage 33 for the working channel is indicated. When the bending section shown in FIG. 5 is bending, the movement will be in a plane perpendicular to the plane of the paper.

FIG. 5 shows one example of a diameter line 35 defined for the bending section. The diameter line is passing through the center axis 17 of the bending section (this cannot be seen from FIG. 5). The diameter line can be placed between two segments to pass both the first and the second hinge. The diameter line 35 is applied for describing the position of the two hinges in relation to a center axis of the bending section, and not to define a measured value of the bending section diameter. The width of the first and second hinges can also be measured along this diameter line.

It is clear from FIG. 5 that the width of the second hinge 24, i.e. the second width, is considerably larger than the width of the first hinge 14, i.e. the first width. Preferably, the width of the second hinge 24 is at least a factor of two larger than the width of the first hinge 14. The second width may be at least a factor of three larger than the first width, and the second width may even be at least a factor of four larger than the first width. Furthermore, the second width is at least 10% of an outer diameter of the bending section, such as at least 15%, or even at least 20% of an outer diameter of the bending section.

The larger width of the second hinge increases the stability of the hinges as such, since the risk of displacement of any of the first hinge and second hinge is reduced by the stronger second hinge. Therefore, the risk that the relatively narrow first hinge will be displaced or even break is also reduced by the introduction of the larger second hinge. Even in the event that the first hinge should be displaced or break, the corresponding larger second hinge will be able to maintain much more stability and functionality in the connection between the two adjacent segments, compared to prior art bending sections.

Figures 6, 7, 8, 9, 10:
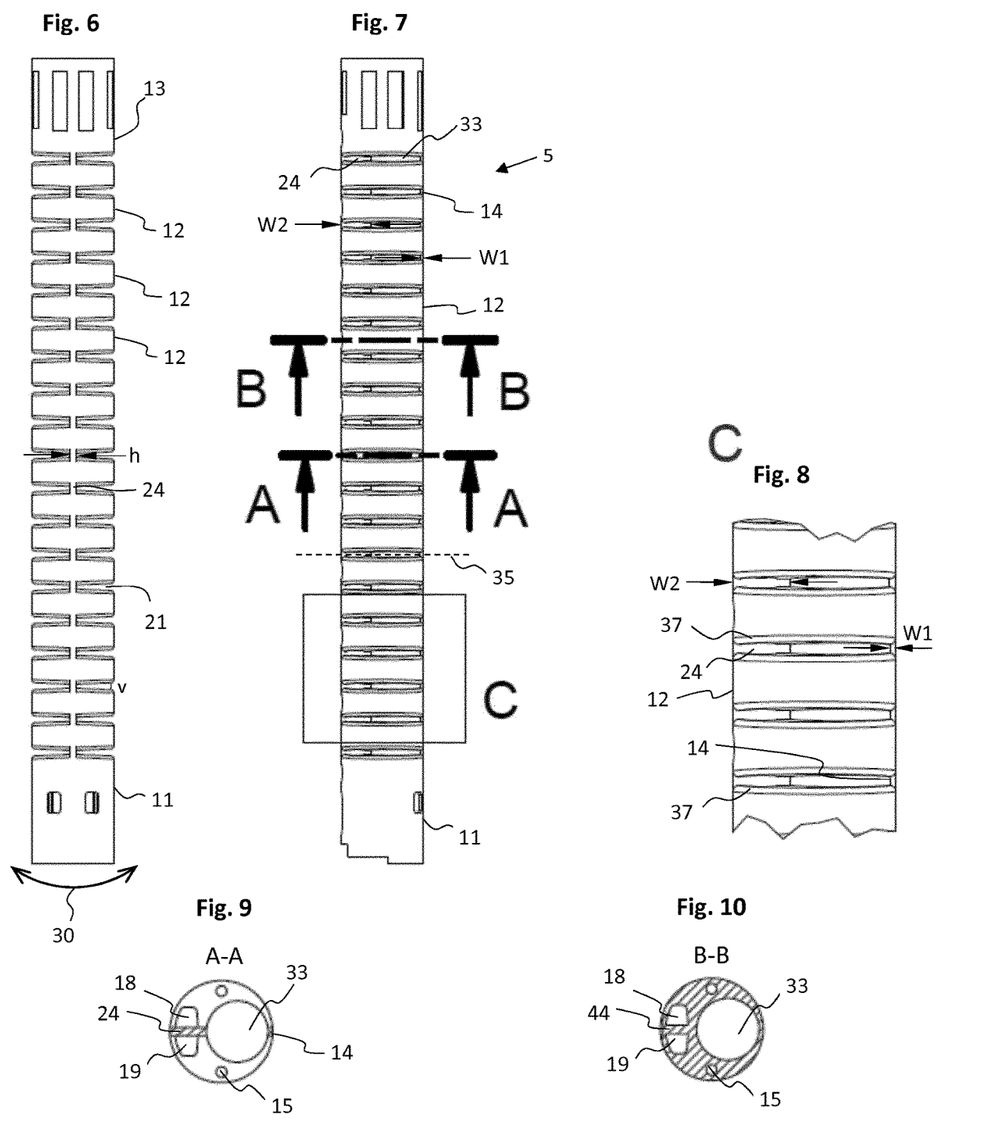
FIG. 6 illustrates a side view of a bending section where the plane with hinges is perpendicular to the plane of the paper, where the bending section is different from the one in FIG. 4.
FIG. 7 illustrates a side view of the bending section of FIG. 6 rotated 90 degrees around a longitudinal axis.
FIG. 8 illustrates an enlarged portion C of the bending section in FIG. 7.
FIG. 9 illustrates the cross-sectional view A-A of the bending section of FIG. 7.
FIG. 10 illustrates the cross-sectional view B-B of the bending section of FIG. 7.

FIGS. 6-10 shows a different example of the bending section, where FIG. 6 illustrates a side view of a bending section where the plane with hinges is perpendicular to the plane of the paper. Here, the angle v is smaller than the angle v in FIG. 4. Also, the height h of the hinges is shown to be the same for all hinges of the bending section, which is different from FIG. 4. FIG. 7 illustrates a side view of the bending section of FIG. 6 rotated 90 degrees around a longitudinal axis. In FIG. 7 two cross sectional cuts A-A and B-B have been indicated. A portion C of the bending section in FIG. 7 have been enlarged and shown in FIG. 8.

In FIG. 8 the first hinge 14 and the second hinge 24 are more clearly seen compared to FIG. 7. It is also shown that the segments 12 are provided with inclined edges 37 towards the space between segments. FIG. 9 illustrates the cross-sectional view A-A between two segments 12 of the bending section in FIG. 7. It is shown by hatching that only the first hinge 14 and the second hinge 24 have been cut through by the cross sectional view A-A. FIG. 10 illustrates the cross-sectional view B-B in the middle of a segment 12 of the bending section in FIG. 7. The hatching shows that both the segment 12 and a continuous rib 44 have been cut through by the cross-sectional view B-B. This continuous rib 44 is formed between the second hinge 24 at the distal end of the segment 12 and the second hinge 24 at the proximal end of the segment.

Figure 11:
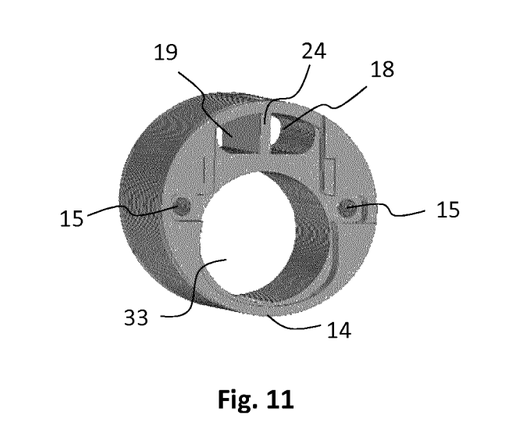
FIG. 11 illustrates a perspective view of a cut through bending section

FIG. 11 shows a perspective view of a cut through bending section, illustrating the first hinge 14 and the second hinge 24 as well as the passage 10 for the working channel and holes 15 for pull wires.

Preferably, the second hinge 24 will separate the two passages 18, 19 along the entire bending section and between all segments 12 of the bending section. This will provide the strongest bending section with a minimum risk of a hinge being displaced.

Figure 12:
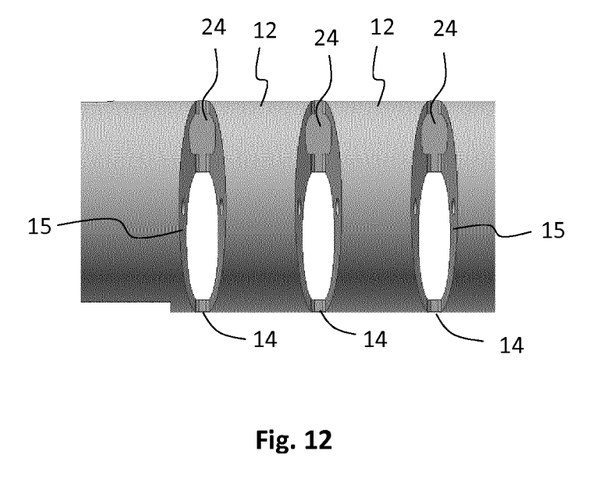
FIG. 12 illustrates another side view of a bending section.

The second width of the second hinge may be constant or approximately constant throughout the bending section or the majority of the bending section. FIG. 12 shows a side view of a bending section where the second width of the second hinge 24 is the same for the second hinges shown.

In an alternative embodiment, the second hinge 24 will only separate the two passages 18, 19 completely for segments arranged in the middle part of the bending section, while there will be an opening through the second hinge between the two passages 18, 19 towards at least one end of the bending section and preferably towards both the distal end and the proximal end of the bending section. This opening will in practice mean that the second hinge is divided into two separate hinges toward the ends of the bending section. One advantage of this embodiment is related to the manufacturing, i.e. the molding, of the bending section.

A fraction of a bending section 5 according to this embodiment is illustrated in FIG. 13 showing the bending section in a side view. In FIG. 13 the second width of the second hinges increases from left to right in the figure. While the second hinge at the left in FIG. 13 has a smaller width, this leaves space for a third hinge between the first hinge 14 and the second hinge 24.

Figure 14:
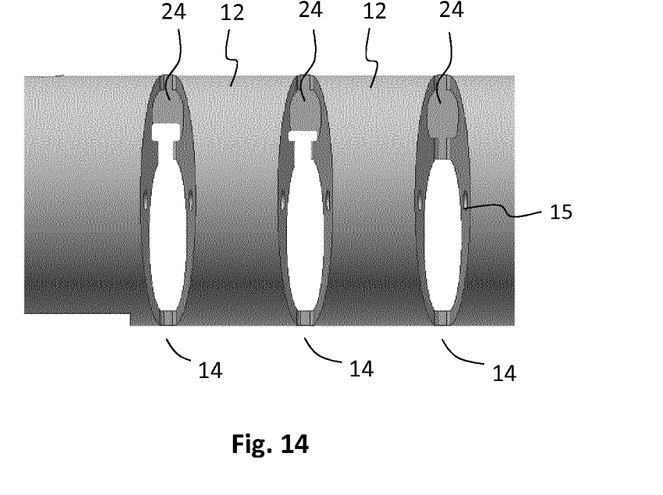
FIG. 14 illustrates a further embodiment of the bending section of FIG. 13.

FIG. 14 shows a further embodiment which does not have a third hinge, but where the second hinge has a variable width. This variable width may imply that the continuous rib is confined by the outer diameter of the bending section and by a line or curve which is not parallel to the center axis of the bending section. The continuous rib will still extend in a plane perpendicular to the bending plane.

The invention claimed is:
1. An endoscope comprising:
   a bending section including:
      segments;
      first hinges disposed on a hinge plane perpendicular to a bending plane of the bending section, each of the first hinges connecting two of the segments that are adjacent to each other;
      a passage extending through the segments and positioned adjacent the first hinges, the passage adapted to receive a working channel tube therein; and
      a rib extending inwardly in the hinge plane and extending longitudinally through the segments, the rib formed in one piece with the segments and the first hinges and positioned adjacent the passage opposite the first hinges, the rib defining second hinges and wall portions, each of the second hinges connecting two of the segments that are adjacent to each other, and each of the wall portions located within each of the segments and connecting two of the second hinges that are adjacent to each other,
   wherein each of the first hinges has a first width along the hinge plane, and
   wherein each of the second hinges has a second width along the hinge plane that is at least twice as long as the first width.

2. The endoscope of claim 1, wherein the hinge plane traverses a center axis of the bending section.

3. An endoscope comprising:
   a bending section including:
      segments;
      first hinges disposed on a hinge plane, each of the first hinges connecting two of the segments that are adjacent to each other;
      a passage extending through the segments and positioned adjacent the first hinges; and
      a rib extending inwardly in the hinge plane from an outer surface of the bending section and extending longitudinally through the segments, the rib positioned adjacent the passage opposite the first hinges and defining second hinges and wall portions between the second hinges, each of the second hinges connecting two of the segments that are adjacent to each other and each of the wall portions connecting two of the second hinges that are adjacent to each other,
   wherein each of the first hinges has a first width along the hinge plane,
   wherein each of the second hinges has a second width along the hinge plane, and
   wherein the second width is at least a factor of two larger than the first width.

4. The endoscope of claim 3, wherein the second width is at least a factor of three larger than the first width.

5. The endoscope of claim 4, wherein the second width is at least a factor of four larger than the first width.

6. The endoscope of claim 3, wherein the bending section has a proximal end and a distal end and extends in a longitudinal direction between the proximal end and the distal end, and wherein the second width varies as a function of a position in the longitudinal direction.

7. The endoscope of claim 6, wherein the second width of a second hinge positioned at the proximal end or the distal end of the bending section is smaller than the second width of a second hinge positioned between the proximal end and the distal end of the bending section.

8. The endoscope of claim 3, wherein the bending section has a proximal end and a distal end and extends in a longitudinal direction between the proximal end and the distal end, wherein the bending section further comprises an intermediate wall section between the rib and the passage, a peripheral wall section, and two passages on opposite sides of the rib between the peripheral wall section and the intermediate wall section, wherein the rib is connected to and extends from the peripheral wall section, wherein a second hinge positioned at the proximal end or the distal end of the bending section is disconnected from the intermediate wall section and a second hinge positioned between the proximal end and the distal end of the bending section is connected to the proximal wall section.

9. The endoscope of claim 8, further comprising a third hinge disposed on the hinge plane between the first hinge and the second hinge, the third hinge extending from intermediate wall sections between adjacent of the segments.

10. The endoscope of claim 1, wherein the bending section including the segments, the first hinges, and the rib, is molded as a one-piece construction of a polymeric material.

11. The endoscope of claim 1, further comprising a working channel accommodated in the passage.

12. The endoscope of claim 1, further comprising a third hinge disposed on the hinge plane between the first hinge and the second hinge.

13. An endoscope system comprising a monitor and an endoscope according to claim 1.

14. An endoscope comprising:
a bending section including:
    segments;
    a peripheral wall, portions of the peripheral wall defining first hinges disposed on a hinge plane perpendicular to a bending plane of the bending section, and each of the first hinges connecting two of the segments that are adjacent to each other;
    a rib connected to and extending inwardly from the peripheral wall in the hinge plane and extending longitudinally through the segments, the rib formed in one piece with the segments and the first hinges opposite the first hinges, the rib defining second hinges and wall portions, each of the second hinges connecting two of the segments that are adjacent to each other, and each of the wall portions located within each of the segments and connecting two of the second hinges that are adjacent to each other,
wherein each of the first hinges has a first width along the hinge plane,
wherein each of the second hinges has a second width along the hinge plane, and
wherein the second width is at least a factor of two larger than the first width.

15. The endoscope of claim 14, wherein the second width is at least a factor of three larger than the first width.

16. The endoscope of claim 15, wherein the second width is at least a factor of four larger than the first width.

17. The endoscope of claim 14, wherein the bending section has a proximal end and a distal end and extends in a longitudinal direction between the proximal end and the distal end, and wherein the second width varies as a function of a position in the longitudinal direction.

18. The endoscope of claim 17, wherein the second width of a second hinge positioned at the proximal end or the distal end of the bending section is smaller than the second width of a second hinge positioned between the proximal end and the distal end of the bending section.

19. The endoscope of claim 18, wherein the bending section further comprises a passage adjacent the first hinges, an intermediate wall section between the rib and the passage, and two passages on opposite sides of the rib between the peripheral wall and the intermediate wall section, wherein the second hinge positioned at the proximal end or the distal end of the bending section is disconnected from the intermediate wall section and the second hinge positioned between the proximal end and the distal end of the bending section is connected to the proximal wall section.

20. The endoscope of claim 19, further comprising a third hinge disposed on the hinge plane between the first hinge and the second hinge, the third hinge extending from intermediate wall sections between adjacent of the segments.

21. The endoscope of claim 14, wherein the bending section including the segments, the first hinges, and the rib, is molded as a one-piece construction of a polymeric material.

22. The endoscope of claim 14, further comprising a third hinge disposed on the hinge plane between the first hinge and the second hinge.

23. The endoscope of claim 1, wherein the bending section has a proximal end and a distal end and extends in a longitudinal direction between the proximal end and the distal end, and wherein the second width varies as a function of a position in the longitudinal direction.

24. The endoscope of claim 1, wherein the bending section further comprises an intermediate wall section between a wall portion of the rib and the passage, a peripheral wall section, and two passages on opposite sides of the wall portion, wherein the wall portion of the rib is connected to and extends from the peripheral wall section to the intermediate wall section.

* * * * *